US010967114B2

(12) United States Patent
Gagel et al.

(10) Patent No.: US 10,967,114 B2
(45) Date of Patent: Apr. 6, 2021

(54) DIALYSIS MACHINE

(71) Applicant: FRESENIUS MEDICAL CARE DEUTSCHLAND GMBH, Bad Homburg (DE)

(72) Inventors: Alfred Gagel, Litzendorf (DE); Pascal Kopperschmidt, Dittelbrunn (DE); Thomas Nuernberger, Burkardroth (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 429 days.

(21) Appl. No.: 15/513,325

(22) PCT Filed: Sep. 25, 2015

(86) PCT No.: PCT/EP2015/001909
§ 371 (c)(1),
(2) Date: Mar. 22, 2017

(87) PCT Pub. No.: WO2016/045798
PCT Pub. Date: Mar. 31, 2016

(65) Prior Publication Data
US 2017/0312417 A1 Nov. 2, 2017

(30) Foreign Application Priority Data
Sep. 19, 2014 (DE) ..................... 10 2014 013 952.2

(51) Int. Cl.
*A61M 1/34* (2006.01)
*A61M 1/36* (2006.01)
(Continued)

(52) U.S. Cl.
CPC ............ *A61M 1/3437* (2014.02); *A61M 1/14* (2013.01); *A61M 1/16* (2013.01); *A61M 1/1607* (2014.02);
(Continued)

(58) Field of Classification Search
CPC .... A61M 2205/276; A61M 2205/3317; A61M 2205/3331; A61M 2205/3334;
(Continued)

(56) References Cited

U.S. PATENT DOCUMENTS

2014/0083943 A1   3/2014 Nuernberger

FOREIGN PATENT DOCUMENTS

WO    WO 03/028860        4/2003
WO    WO-03028860 A1 *    4/2003    .............. A61M 1/16
(Continued)

*Primary Examiner* — Robert Clemente
*Assistant Examiner* — Akash K Varma
(74) *Attorney, Agent, or Firm* — Jacobson Holman PLLC

(57) ABSTRACT

A dialysis machine has a blood circuit, a blood pump, a dialyzer, a venous pressure sensor, a substituate line, and a control unit. The control unit can operate the blood pump in a first operating mode and in a special operating mode, and start the special operating mode after a trigger event. In the special operating mode, a blood pump conveying rate is controlled via a default value or regulated to a desired value, with the default or desired value being derived from a value determined before the started special mode or corresponding to the value. The presence of an obstacle is polled before the special mode, and depending on the presence thereof, the start of the special mode is blocked or delayed and/or the selection of the default value or the desired value on the presence of the obstacle differs from the selection without the presence of the obstacle.

19 Claims, 3 Drawing Sheets

(51) Int. Cl.
  *A61M 1/26* (2006.01)
  *A61M 1/16* (2006.01)
  *A61M 1/14* (2006.01)
(52) U.S. Cl.
  CPC .......... *A61M 1/1617* (2014.02); *A61M 1/267* (2014.02); *A61M 1/34* (2013.01); *A61M 1/341* (2014.02); *A61M 1/3406* (2014.02); *A61M 1/3413* (2013.01); *A61M 1/3609* (2014.02); *A61M 1/3639* (2013.01); *A61M 2202/0413* (2013.01); *A61M 2205/276* (2013.01); *A61M 2205/3317* (2013.01); *A61M 2205/3331* (2013.01); *A61M 2205/3334* (2013.01); *A61M 2205/3344* (2013.01); *A61M 2205/3355* (2013.01); *A61M 2205/3365* (2013.01); *A61M 2205/50* (2013.01); *A61M 2205/6018* (2013.01); *A61M 2230/207* (2013.01); *A61M 2230/30* (2013.01)
(58) Field of Classification Search
  CPC .. A61M 2205/3344; A61M 2205/3355; A61M 2205/3365; A61M 2205/50; A61M 2205/6018; A61M 2230/207; A61M 2230/30; A61M 2202/0413; A61M 1/3437; A61M 1/1607; A61M 1/1617; A61M 1/267; A61M 1/3406; A61M 1/341; A61M 1/3609; A61M 1/14; A61M 1/16; A61M 1/34; A61M 1/3413; A61M 1/3639; A61M 1/36; A61M 1/26
  USPC ....................................................... 210/96.2
  See application file for complete search history.

(56) References Cited

FOREIGN PATENT DOCUMENTS

| | | |
|---|---|---|
| WO | WO 2009/144522 | 12/2009 |
| WO | WO-2009144522 A1 * | 12/2009 ............ A61M 1/342 |

* cited by examiner

DIALYSIS MACHINE

BACKGROUND OF THE INVENTION

1. Field of the Invention

The invention relates to a dialysis machine having an extracorporeal blood circuit, a blood pump, a dialyzer, a pressure sensor for measuring the fluid pressure in the extracorporeal blood circuit, a line for the supply of substitution fluid into the extracorporeal blood circuit, and a control unit.

2. Description of Related Art

Dialysis processes are known in the prior art in which a specific volume of plasma is removed from the patient's blood on the basis of a fluid convection through the dialyzer membrane. These processes include hemodiafiltration and hemofiltration. To prevent thickened blood from being conducted back to the patient in these processes, substitution fluid (substitute) is continuously supplied into the extracorporeal blood circuit.

If the supply of substitute stops or is reduced at least temporarily for specific reasons, thickened blood flows through the venous line of the extracorporeal blood circuit and the venous connection. Frequent reasons for an at least temporary stopping or reduction of the supply of substitute comprise e.g. a change of the UF rate or a switchover from hemodiafiltration to hemodialysis during an ongoing treatment. Further reasons comprise e.g. the carrying out of a pressure holding test, a safety shut-off of the substitute supply or a swapping of the concentrate containers.

The fluid pressure (i.e. the blood pressure) in the extracorporeal blood circuit temporarily increases due to the higher viscosity of the thickened blood. This can, for example, result in a pressure alarm and is unwanted.

Against this background, it is known from WO 2009/144522 A1 to provide, in addition to the normal operation of the blood pump in which the blood pump is operated e.g. at a specific desired conveying rate, a special operating mode of the blood pump in which the conveying rate is regulated in dependence on the venous pressure. The special operating mode starts after a trigger event and ends after the elapse of a certain length of time. The trigger event is related to a reduction of the substitute supply. For example, a trigger event is present when the venous pressure, the conveying rate of the substitute pump or the variation of these values exceeds or falls below a specific threshold value. It can be achieved in this manner in a special operating mode that the conveying rate of the blood pump is temporarily reduced when a threshold value of the venous pressure is exceeded or threatens to be exceeded.

In such a regulation, problems can, however, occur when a further trigger event occurs still during the special operating mode or if only a little time elapses between the end of the special operating mode and the next trigger event. For the desired value of the venous pressure at which the actual venous pressure is oriented during the special operating mode is derived from the measured venous pressure before the trigger event. In the special operating mode, this can be subject to greater variations than in normal operation due to a certain inertia of the system and only stabilizes after the elapse of a certain time after the end of the special operating mode. An unsuitable desired value can thus be assumed if a triggering of a further episode of the special operating mode occurs in this phase.

This can, for example, result in a repeat self-triggering of the special operating mode. For if an incorrect desired value is assumed in the special operating mode, the conveying rate of the blood pump differs greatly from the desired conveying rate for normal operation and changes abruptly after the end of the special mode. This change in the conveying rate can bring about a further trigger event, for example a brief peak in the venous pressure or—provided it is coupled to the conveying rate of the blood pump—in the conveying rate of the substitute pump and the repeat assumption of an incorrect desired value for the venous pressure in the special mode is probable.

It can furthermore be an effect that a frequent triggering of a pressure alarm occurs since, on a regulation by an incorrect desired value, a limit value for triggering the alarm determined in the normal mode is more frequently fallen below or exceeded.

SUMMARY OF THE INVENTION

It is the object of the present invention to reduce the risk that an unsuitable default value for a control or an unsuitable desired value for a regulation of the blood pump is assumed in the special mode.

Against this background, the invention relates to a dialysis machine which has an extracorporeal blood circuit, a blood pump, a dialyzer, a venous pressure sensor for measuring the venous pressure in the extracorporeal blood circuit and a line for the supply of substitute into the extracorporeal blood circuit. The dialysis machine furthermore has a control unit which is configured to operate the blood pump in a first operating mode and in a special operating mode and to start the special operating mode after recognition of a trigger event. In the special operating mode, a conveying rate of the blood pump is controlled using a default value or is regulated to a desired value, with the default value or the desired value corresponding to or being derived from a value determined before the start of the currently started special operating mode or of the special operating mode to be started by the current trigger event.

Provision is made in accordance with the invention that the control unit is furthermore configured such that the presence of at least one obstacle is polled before the start of the special operating mode. On the presence of the obstacle, the start of the special operating mode is blocked or delayed. Alternatively or additionally, if the obstacle is present, the selection of the default value or of the desired value differs from the corresponding choice in the hypothetical case of a missing presence of the obstacle.

The (measured) value which was determined before the start of the currently started special operating mode and which corresponds to the default value or to the desired value or is derived from the default value or desired value, can relate to a property of the blood in an embodiment. Examples comprise a blood viscosity or a hematocrit portion. In a further embodiment, the measured value on whose basis the default value or the desired value is determined can be an instrument value. Examples comprise a motor current draw or a motor power draw of the blood pump. A preferred example comprises the venous pressure. The desired value or the default value which can be derived from this value can likewise comprise these parameters. The derivation of a default value or of a desired value in the form of one of these parameters, for example a motor performance draw, from a measured value in the form of another of these parameters, e.g. of the venous blood pressure, is conceivable and covered by the invention.

Provision can, for example, be made that the conveying rate of the blood pump is lowered in the special operating mode when the measured venous pressure exceeds the desired value and that the conveying rate of the blood pump is increased in the special operating mode when the measured venous pressure lies below the desired value. Provision can alternatively be made that the control unit uses a default value for controlling the blood pump in the special operating mode which corresponds to a value or which was derived from a value which was measured or determined directly before the start of the special mode (e.g. venous pressure or motor current power draw).

In an embodiment an obstacle comprises the blood pump currently already being operated in the special mode. Provided that in this case the selection of the default value or of the desired value differs from the normal case on the presence of the obstacle, the default value or the desired value can be taken over from the existing special operating mode on the presence of the obstacle.

In an embodiment, at least one of the obstacles comprises a specific waiting period after the start or the elapse of a phase which is deployed beforehand in time and in which the blood pump was operated in the special operating mode not yet having been reached. Provided that in this case the selection of the default value or of the desired value on the presence of the obstacle differs from the selection without the presence of the obstacle, the default value or the desired value can be taken over from the special operating mode during the phase deployed beforehand in time. The duration of the waiting period can correspond to the forecast flow time of the blood through the venous line of the extracorporeal blood circuit or can be orientated thereon, e.g. with a percentage deduction or addition (10%, 20%, 30%, 50%, etc.). It is furthermore conceivable that the waiting period is rigidly fixed by a user input or by a default value on the machine side or is based on a specific volume throughput of the blood pump.

Alternatively to the end of the phase deployed beforehand in time, the start of the phase deployed beforehand in time can also be used as the starting point of the waiting period. It is furthermore conceivable that an event of the treatment is used as the starting point of a waiting period which is independent of a phase which was deployed beforehand in time and in which the blood pump was operated in the special operating mode. This, for example, includes a point in time in which a measured value (e.g., for example, the first time derivation of the venous pressure) exceeds a threshold value or in which a certain spacing of a measured value (e.g. the venous pressure) from the expected value is present.

In an embodiment, an obstacle comprises the first time derivation of the venous pressure exceeding a threshold value on the presence of the trigger event. This is equivalent to an unstable state in which no suitable default value or no suitable desired value can be determined. In this case, too, either the triggering of the special operating mode is blocked or the default value or the desired value is adopted for the new special operating mode from the special operating mode deployed beforehand in time.

A displacement of the triggering of the special operating mode is a subcase of the blocking since a blocking of the triggering can result in a displacement of the triggering when the trigger event is maintained (and continues to be polled periodically or continuously) and the obstacle is removed.

A plurality of obstacles can be polled in a cumulative manner. It is furthermore conceivable that only one or two obstacles are polled.

In an embodiment, the default value or the desired value is derived from the measured value, for example from the venous pressure before starting the special mode. For example, a measured value of the venous pressure within the last 60, 30 or 10 seconds before the occurrence of the trigger event or of the start of the special operating mode can be assumed, optionally more than 1 second before or also less than 1 second before the occurrence of the trigger event or the start of the special operating mode. The assumption of a mean value from a plurality of measured values determined in this period is also conceivable.

In an embodiment, the blood pump is operated at a predefined flow rate development, in particular at a constant flow rate or at a constant speed, before and/or after the special operating mode.

The trigger event can, for example, be the exceeding or the falling below of an expected value for the measured value, for example the venous pressure. This can, for example, be related to a reduction in the ultrafiltration rate or to a switchover from hemodiafiltration to hemodialysis when the addition of substituate is restricted or set, but thickened blood is still present in a line section upstream of the opening point for the substituate line and downstream of the dialyzer. Furthermore, this can be related to an interruption of the substituate supply, for example within the framework of a carrying out of a pressure holding test of the substituate circuit, of a safety shut-down of the substituate supply (e.g. detection of a conductivity fluctuation or of air bubbles in the substituate) or of a swapping of the concentrate containers. The venous pressure can be reduced if more highly diluted blood is located in at least one section of the venous line. This can, for example, be related to a reduction in the ultrafiltration rate or of the transmembrane pressure or to a switchover from hemodialysis to hemodiafiltration when the addition of substituate is restricted or set, but less greatly thickened blood is still present in a line section upstream of the opening point for the substituate line and downstream of the dialyzer. Furthermore, this can be related to a bolus delivery by substituate into the extracorporeal blood circuit to be able to carry out specific measurement processes, for example.

The trigger event can furthermore be a stop, a reduction, a start or an increase in the substituate administration. This can be in the same relation as was discussed above regarding the trigger event of the exceeding or falling below of a threshold value for the venous pressure. Furthermore, the conveying rate of a substituate pump located in the substituate line and responsible for the conveying of the substituate into the extracorporeal blood circuit is frequently coupled to the conveying rate of the blood pump so that treatment-induced changes in the conveying rate of the blood pump can also trigger such an event.

The special operating mode can last so long until it is manually ended by the user. Provision can alternatively or additionally be made that the duration of the special operating mode is approximated to or is orientated on the forecast flow time of the blood through the venous line of the extracorporeal blood circuit under the normal operation of the blood pump. This duration can, for example, be assumed or a security addition of at least 10%, 20% or 50%, but optionally of less than 100%, can be added. A forecast of the flow time of the blood through the venous line of the extracorporeal blood circuit under the normal operation of the blood pump can take place, for example, on the basis of the conveying rate of the blood pump before the start of the special operating mode and of the known construction type of the extracorporeal blood circuit (length, diameter, total volume of the individual sections, etc.). Typical forecast time durations comprise, for example, time periods of between 1 and 10 minutes or of between 10 and 60 seconds or also of between 1 and 10 seconds.

It is furthermore conceivable that the control unit is configured such that the waiting period correlates with the duration of the special operating mode.

In an embodiment, the line for the supply of substituate opens into the venous line of the extracorporeal blood circuit. It is therefore a line for the postdilution. The line can open into the extracorporeal blood circuit upstream or downstream of the pressure sensor. Provision can alternatively also be made that the line for the supply of substituate opens in the arterial line of the extracorporeal blood circuit. The changes of the venous pressure caused by fluctuations in the predilution are, however, generally lower than the changes of the venous pressure caused by fluctuations in the postdilution.

The line for supplying the substituate can comprise a substituate pump which is responsible for the conveying of the substituate into the extracorporeal blood circuit.

In an embodiment, a change in the supply rate of the substituate is blocked or is only allowed within a predefined range during the course of the special operating mode. This measure can prevent the occurrence of trigger events during the special mode, for example a falling below of the pressure limits. For example, a bolus delivery during the special mode can be blocked in this manner. Furthermore this measure can prevent the occurrence of trigger events at the end of the special mode. For an increase in the substitution rate during the special operating mode results in a lower pressure and in an increase in the conveying rate of the blood pump by the blood dilution. This conveying rate would then be abruptly changed at the end of the special operating mode.

In an embodiment, a change in the supply of the substituate is blocked or is only permitted within a predefined range within a specific waiting period after the end of the special operating mode. This measure can prevent the occurrence of trigger events directly after the end of the special mode. The occurrence of unwanted pressure alarms can also be prevented since large changes of the ratio of the substitution rate to the blood flow can be prevented. The duration of the waiting period can correspond to the forecast flow time of the blood through the venous line of the extracorporeal blood circuit or can be orientated thereon, e.g. with a percentage deduction or addition (10%, 20%, 30%, 50%, etc.). It is furthermore conceivable that the waiting period is rigidly fixed by a user input or by a default value on the machine side or is based on a specific volume throughput of the blood pump.

The configuration of the control unit in accordance with the invention is based on the fact that the control unit is connected to the relevant components of the dialysis machine and that an algorithm is stored in the control unit which allows the control of the blood pump in accordance with the invention.

BRIEF DESCRIPTION OF THE DRAWINGS

Further details and advantages of the invention result from the following discussed Figures and embodiments. There are shown in the Figures.

DETAILED DESCRIPTION OF THE PREFERRED EMBODIMENTS

Figure 1:
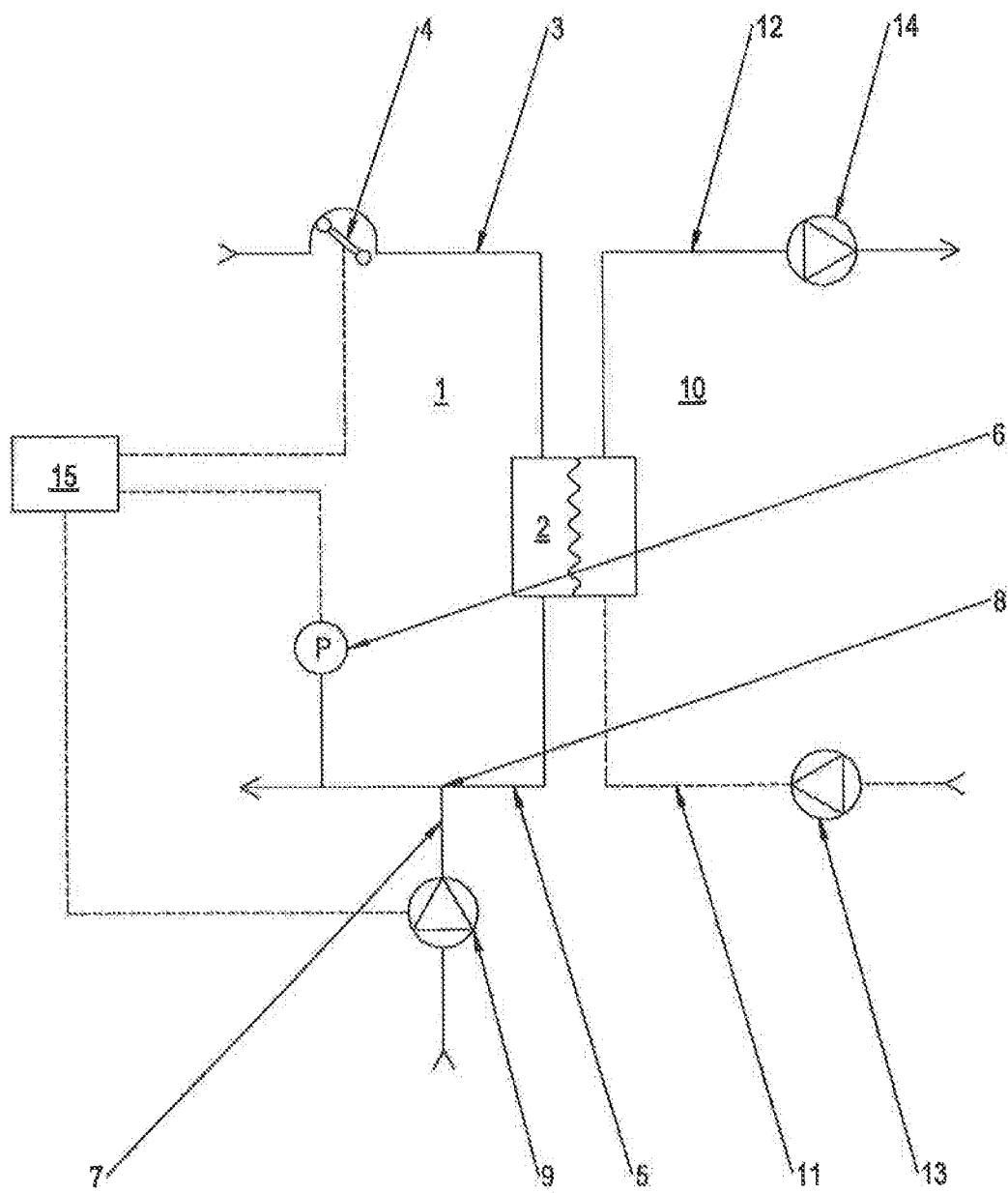
FIG. 1: a schematic representation of a dialysis machine in accordance with the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description, FIG. 1 shows a schematic representation of a dialysis machine in accordance with the invention. This dialysis machine has an extracorporeal blood circuit 1 and a dialyzer 2. The dialyzer 2 can, for example, be a hollow fiber dialyzer.

The blood pump 4 is located in the arterial line 3 of the extracorporeal blood circuit 1. The blood pump 4 can, for example, be a peristaltic pump. A venous pressure sensor 6 is located in the venous line 5 of the extracorporeal blood circuit. Furthermore, a postdilution line 7 is provided which opens into the venous line 5 of the extracorporeal blood circuit upstream of the venous pressure sensor 6 at the opening point 8. The substituate pump 9 is located in the postdilution line 7.

The extracorporeal blood circuit 1 is in communication with the dialyzing fluid circuit (dialyzate circuit) 10 via the membrane arranged in the dialyzer 2. The shown embodiment of the dialysis machine can be configured in dependence on the device setting for carrying out a hemodialysis, a hemodiafiltration or a hemofiltration. In the case of hemodialysis and hemodiafiltration, the dialyzate side of the dialyzer 2 is fed with fresh dialysis fluid via the part 11 of the dialyzate circuit 10 located upstream of the dialyzer 2. Consumed dialyzate and, where applicable, ultrafiltrate flow off via the part 12 of the dialyzate circuit 10 located downstream of the dialyzer 2. In the case of hemofiltration, a feed of the dialyzate side of the dialyzer 2 with dialyzing fluid is omitted and only ultrafiltrate is led off via the part 12 of the dialyzate circuit 10 located downstream of the dialyzer 2. Since the part 11 of the dialyzate circuit 10 located upstream of the dialyzer 2 is not used in every operating form of the machine, it is only shown in dotted form in the Figure. In the embodiment shown, dialyzate pumps 13 and 14 are arranged in the dialyzate circuit 10 both upstream and downstream of the dialyzer 2. A different arrangement of these pumps or an omission of at least one of these pumps is, however, naturally also conceivable.

The postdilution line 7 branches off either from the part 11 of the dialyzate circuit 10 upstream of the dialyzer 2 and thus obtains the substituate from this line or leads to a separate reservoir, not shown in any more detail, for the substituate.

The control unit 15 in the shown embodiment communicates with the blood pump 4, with the venous pressure sensor 6 and with the substituate pump 9. It regulates the conveying rate of the blood pump 4 and receives signals of the venous pressure sensor 6. In normal operation, the control unit 15 regulates the blood pump 4 such that a specific conveying rate for the blood is selected. The conveying rate is selected, for example, such that the transmembrane pressure at the dialyzer 2 allows a reaching of the treatment goals. Details on the selection of the conveying rate in normal operation are known in the prior art and are not a subject of the present patent application.

An algorithm is stored in the control unit 15 which starts a so-called special operating mode of the blood pump 4 temporarily after recognition of a trigger event. In this special operating mode, the conveying rate of the blood pump is regulated in dependence on the venous pressure determined at the venous pressure sensor 6, and indeed such that the measured venous pressure is compared with a desired value and the pump is regulated in dependence on the result of this comparison. The conveying rate of the blood pump is thus reduced in the special operating mode when the measured venous pressure exceeds the desired value and it is increased when the measured venous pressure is below the desired value.

This embodiment therefore describes a regulation of the pump rate on the basis of the venous pressure. The invention is, however, naturally not restricted to the adoption of the venous pressure as the desired value. The invention is furthermore naturally not restricted to the regulation, but can rather also comprise a control instead of the regulation which uses a default value, for example a venous pressure or a motor power draw of the blood pump directly before the special mode, for determining the pump rate. The indications made in connection with the embodiment can naturally also be applied to these alternative embodiments.

In the present embodiment, the desired value is derived from a pressure measured before the start of the special mode at the venous pressure sensor 6. For example, a single value measured 1 second before the start of the special mode at the venous pressure sensor 6 can be used as the desired value, with this only being by way of example and with this selection of the desired value not representing a necessary component of the present embodiment.

In the present embodiment, an exceeding or falling below of a threshold value for the pressure measured at the venous pressure sensor 6 is assumed to be a trigger event. This choice is likewise only by way of example and does not represent a necessary component of the present embodiment. It would equally be conceivable that the control unit 15 is furthermore in communication with the substitute pump 9 and that a stop, a reduction, a start or an increase in the substitute administration is selected as the trigger event. These events, for example, correspond to a slowing down of the substitute pump 9, e.g. on a clogging (often also called a clotting) of the dialyzer 2, or to a stopping of the substituate pump 9 without effects on the blood pump 4, e.g. when a pressure holding test of the hydraulics takes place, alarms of the substitute supply are triggered (conductivity or temperature of the dialyzate, unphysiological) or a change of the treatment type takes place (hemodiafiltration after hemofiltration, hemodiafiltration after hemofiltration, or vice versa).

The duration of the special operating mode corresponds in the present embodiment to the forecast flow time of the blood—while assuming the conveying rate before the start of the special operating mode—through the venous line plus a safety addition of 30%. This choice is likewise by way of example and does not represent a necessary component of the present embodiment.

Provision is also made in accordance with the invention that the control unit carries out a further polling using the stored algorithm after a recognition of the trigger event before the special operating mode of the blood pump 4 is started. This poll is directed to whether an obstacle is present which speaks against the starting of the special model or at least requires an adaptation in the selection of the desired value.

Such an obstacle comprises the blood pump 4 currently already being operated in the special mode. In this case, the duration of the special operating mode is admittedly extended and to this extent a further special operating mode is started. However, the desired value for the venous pressure is not fixed on the basis of a measured value for the venous pressure determined during the existing special operating mode—and thus 1 second before the start of the further special operating mode—but the desired value is rather taken over from the existing special operating mode.

A further obstacle comprises the blood pump 4 only running in normal operation for a short period, for example because a phase has just ended in which the blood pump was operated in the special operating mode. To this extent, this obstacle, for example, comprises a sequence of two phases which are too close in time and in which the blood pump 4 is operated in the special operating mode. In this case, either the triggering of the special operating mode is blocked or the desired value is adopted for the new special operating mode from the special operating mode deployed beforehand in time. The duration of the waiting period is selected in the present embodiment such that it corresponds to the forecast flow time of blood through the venous line of the extracorporeal blood circuit. The flow time is forecast with reference to the conveying rate of the blood pump before the start in the (past) special operating mode and to the known construction type of the venous line. This choice is by way of example and does not represent a necessary component of the present embodiment. For example, a specific volume flow through the blood pump 4 can also simply be used or also a fixed time duration can simply be used.

A further obstacle comprises the first time derivation of the venous pressure exceeding a threshold value on the presence of the trigger event, i.e. when a strong drift is present and the system is not stable. Provided that this is the case, it is questionable whether a suitable desired value can be determined. In this case, too, either the triggering of the special operating mode is blocked or the desired value is adopted for the new special operating mode from the special operating mode deployed beforehand in time.

The blocking of the triggering of the special operating mode can as a result also lead to a displacement of the triggering of the special operating mode, namely when the trigger event (e.g. the exceeding of the limit value for the venous pressure) is maintained and the obstacle is removed.

In the present embodiment, these obstacles are cumulatively polled; however, it is also conceivable and covered by the invention if only one or two of these obstacles are polled.

Figure 2:
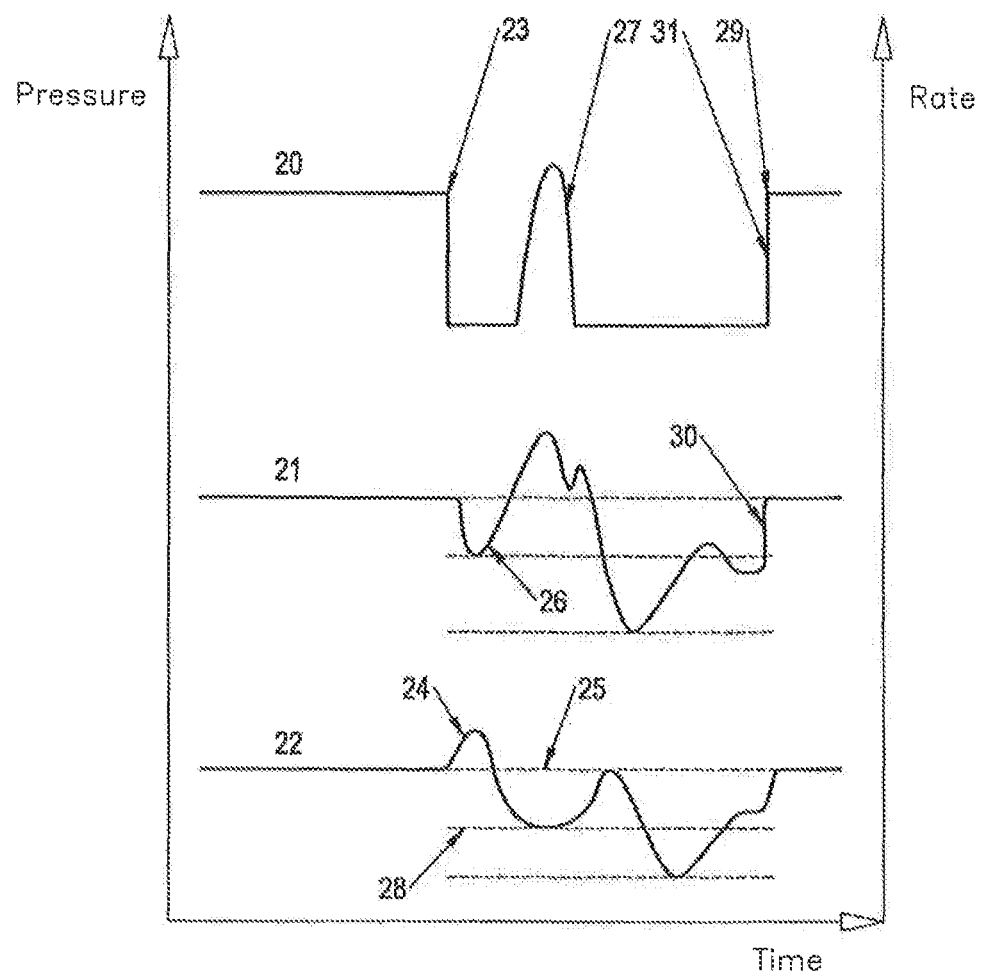
FIG. 2: a schematic representation of the time development of the conveying rate of the substituate pump, of the conveying rate of the blood pump and of the venous pressure in a dialysis machine in accordance with the prior art.

FIG. 2 shows a schematic representation of the time development of the conveying rate of the substitute pump 20, of the conveying rate of the blood pump 21 and of the venous pressure 22 in a dialysis machine in accordance with the prior art. The dialysis machine can have the same elements from a construction aspect as was explained in connection with FIG. 1. With respect to the invention, there is only a lack of the configuration of the control unit such that it carries out still another polling after the recognition of the trigger event before the special operating mode of the blood pump is started.

As can be seen from the Figure, a change in the substitution rate is used as the trigger event in the example shown from the prior art (reference numeral 23). For example, in the present case, a pressure holding test of the substituate system results in a triggering of the special operating mode. The failure of the substitution results in the presence of thicker blood in the venous line and in an increase in the venous pressure (reference numeral 24). Since the blood pump is, however, controlled in the special mode in dependence on the venous pressure such that a remaining of the venous pressure at the desired value is desired (reference numeral 25), the conveying rate of the blood pump (reference numeral 26) falls as the venous pressure increases. The desired value is fixed with reference to the venous pressure before the start of the special mode in the prior art. As can be recognized from the curves 21 and 22, the pressure development is subject to a specific inertia during the special operating mode. The actual venous pressure in this respect fluctuates about the desired value.

If now a further trigger event occurs while the special operating mode is still present (for example, in the form of a bolus delivery, reference numeral 27), a new special mode is started. This special mode differs from the existing special mode by the magnitude of the desired value which is fixed with reference to the venous pressure before the start of the current further special mode (reference numeral 28). However, due to the above-described fluctuation, this desired value differs to a significant degree from the venous pressure which would be expected in normal operation of the blood pump. To this extent, with regard to the Figures, a falling of the blood pump rate takes place to the bottommost dashed line, which also results in a falling of the venous pressure to the dashed line. For it is not the initial value before the first event which is adopted as the desired value, which would be correct, but rather that which is incorrectly adopted as the starting value by the system, that is in accordance with FIG. 2 that value on the middle line of the curve 21.

This has the result that the blood pump rate increases greatly (reference numeral 30) at the end of the special mode (reference numeral 29). Since the rate of the substituate pump in the system is coupled to the rate of the blood pump in accordance with FIG. 2, the rate of the substitution pump also increases abruptly at the end of the special operating mode (reference numeral 31). This can result in an unwanted self-triggering of the special mode.

Figure 3:
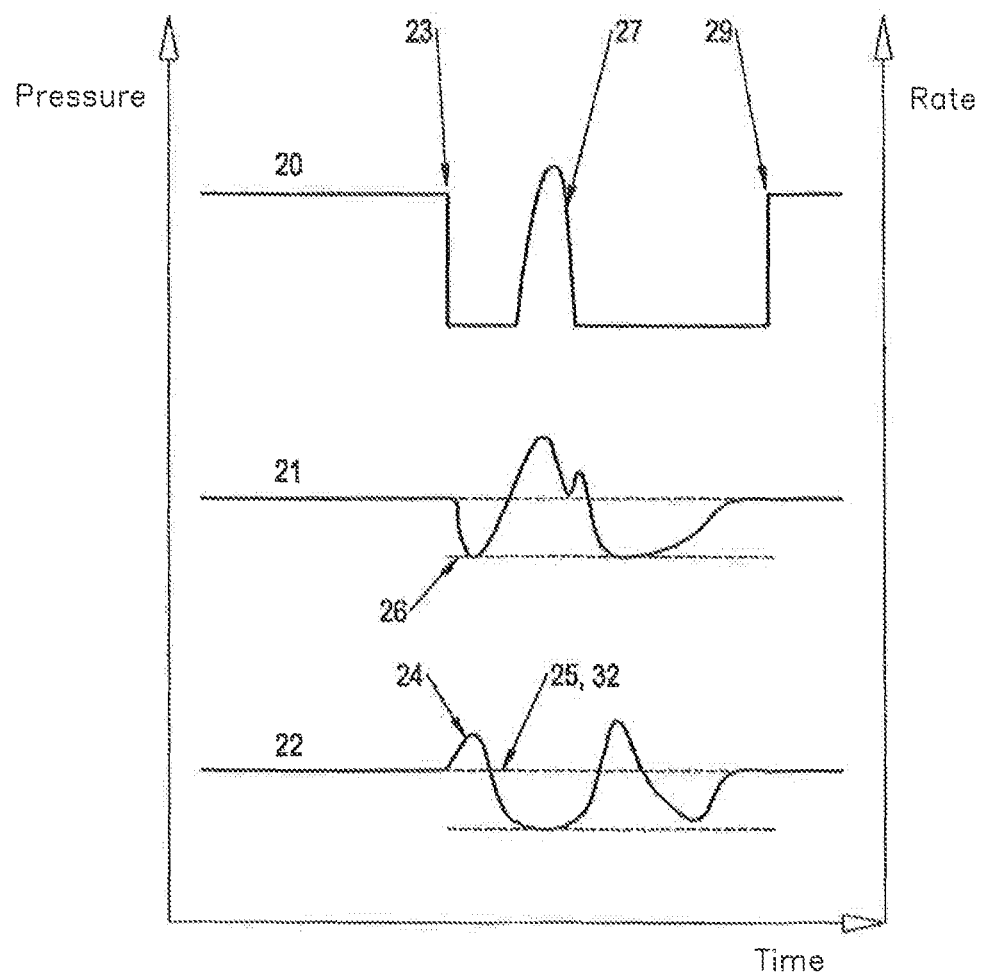
FIG. 3: a schematic representation of the time development of the conveying rate of the substituate pump, of the blood pump and of the venous pressure in a dialysis machine in accordance with the invention.

FIG. 3 shows a schematic representation of the time development of the conveying rate of the substituate pump 20, of the conveying rate of the blood pump 21 and of the venous pressure 22 in a dialysis machine in accordance with the invention. The dialysis machine has the identical structure to the dialysis machine on which the representation in accordance with FIG. 2 is based. Provision is only made here that the control unit carries out a further polling after a recognition of the trigger event before the special operating mode of the blood pump is started.

In FIG. 3, corresponding reference numerals are used for corresponding events or features with respect to FIG. 2. The associated explanation can also be taken over accordingly.

As can be recognized with reference to the Figure, a polling is carried out after the presence of an obstacle after the recognition of the second trigger event (reference numeral 27) by the control unit before the start of a further special mode. Such an obstacle is recognized such that the blood pump is currently already being operated in the special mode. As a result of this, a new desired value is not selected for the venous pressure for the second special mode as was the case in FIG. 2 (there: reference numeral 28), but the desired value is rather taken over from the existing special operating mode (reference numeral 32). This desired value approximately corresponds to the venous pressure which would be expected in the normal operation of the blood pump. This has the result that at the end of the special mode no significant change of the conveying rate of the blood pump is required and an unwanted self-triggering of the system is avoided.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialysis machine comprising:
   an extracorporeal blood circuit, a blood pump, a dialyzer, a venous pressure sensor, a substituate line, and a control unit,
   the control unit being configured to operate the blood pump in a first operating mode and in a special operating mode, and to start the special operating mode after recognition of a trigger event,
   with, in the special operating mode, a conveying rate of the blood pump being controlled via a default value, or being regulated to a desired value, the default value or the desired value being derived from a value determined before the start of the started special operating mode or corresponding to said value,
   the control unit being configured to poll a presence of an obstacle before the start of the special operating mode, the obstacle including a specific waiting period, a duration of which has not been achieved, after a start or an elapse of a phase which is deployed earlier in time and in which the blood pump is operated in the special operating mode, and
   on a determination of the presence of the obstacle, to at least one of (i) block or delay the start of the special operating mode and (ii) make the selection of the default value or of the desired value on the presence of the obstacle differ from the selection without the presence of the obstacle.

2. The dialysis machine in accordance with claim 1, wherein the value determined before the start of the started special operating mode, the desired value, or the default value, is a blood property, or an instrument value, or a venous pressure.

3. The dialysis machine in accordance with claim 1, wherein the obstacle includes the blood pump already being operated in the special operating mode.

4. The dialysis machine in accordance with claim 3, wherein the default value or the desired value is taken over from an existing special operating mode when the blood pump is already being operated in the special operating mode.

5. The dialysis machine in accordance with claim 1, wherein the default value or the desired value is taken over from the special operating mode during the phase deployed earlier in time.

6. The dialysis machine in accordance with claim 1, wherein the obstacle includes a first time derivation of a measured value on the presence of the trigger event that exceeds a threshold value.

7. The dialysis machine in accordance with claim 1, wherein the default value or the desired value is derived from the measured value before starting the special operating mode.

8. The dialysis machine in accordance with claim 1, wherein the control unit is configured such that the blood pump is operated at least one of before and after the special operating mode at a predefined flow rate development.

9. The dialysis machine in accordance with claim 1, wherein the trigger event is at least one of the exceeding or falling below of a threshold value or gradient for a measured value, and a stop, a reduction, a start, or an increase in administration of a substituate.

10. The dialysis machine in accordance with claim 1, wherein the control unit is configured such that a duration of the special operating mode is approximated to or orientated on a forecast flow time of blood through a venous line of the extracorporeal blood circuit under normal operation of the blood pump.

11. The dialysis machine in accordance with claim 1, wherein the control unit is configured such that the waiting period correlates to a duration of the special operating mode.

12. The dialysis machine in accordance with claim 1, wherein the substituate line opens into the venous line of the extracorporeal blood circuit.

13. The dialysis machine in accordance with claim 1, wherein the control unit is configured such that, during operation of the special operating mode, a change in a supply rate of the substituate is blocked or is only permitted within a predefined range.

14. The dialysis machine in accordance with claim 1, wherein the control unit is configured such that, within a certain waiting period after an end of the special operating mode, a change in a supply of the substituate is blocked or is only permitted within a predefined range.

15. The dialysis machine according to claim 2, wherein the blood property is a blood viscosity or a hematocrit portion, and the instrument value is a motor current draw or a motor power draw of the blood pump.

16. The dialysis machine according to claim 6, wherein the measured value is a venous pressure.

17. The dialysis machine according to claim 7, wherein the measured value is a venous pressure.

18. The dialysis machine according to claim 8, wherein the predefined flow rate development is at a constant flow rate or at a constant speed.

19. The dialysis machine according to claim 9, wherein the measured value is a venous pressure.

* * * * *